(12) United States Patent
Murata et al.

(10) Patent No.: US 8,119,373 B2
(45) Date of Patent: Feb. 21, 2012

(54) METHOD FOR PURIFYING HISTIDINE FROM A CELL CULTURE

(75) Inventors: Hideki Murata, Yamaguchi (JP); Noboru Fujii, Ibaraki (JP); Kenji Tajima, Yamaguchi (JP)

(73) Assignee: Kyowa Hakko Bio Co., Ltd. (JP)

( * ) Notice: Subject to any disclaimer, the term of this patent is extended or adjusted under 35 U.S.C. 154(b) by 607 days.

(21) Appl. No.: 12/282,815

(22) PCT Filed: Mar. 15, 2007

(86) PCT No.: PCT/JP2007/055190
§ 371 (c)(1),
(2), (4) Date: Oct. 10, 2008

(87) PCT Pub. No.: WO2007/119369
PCT Pub. Date: Oct. 25, 2007

(65) Prior Publication Data
US 2009/0130723 A1 May 21, 2009

(30) Foreign Application Priority Data
Mar. 15, 2006 (JP) ................................ 2006-071576

(51) Int. Cl.
*C12P 13/24* (2006.01)
(52) U.S. Cl. ..... 435/107; 435/170; 435/171; 435/252.1; 435/252.8

(58) Field of Classification Search .................. 435/107, 435/170, 171, 252.1, 252.8
See application file for complete search history.

(56) References Cited

U.S. PATENT DOCUMENTS

| 5,300,653 A * | 4/1994 | Nozaki et al. ................. 548/497 |
|---|---|---|
| 2002/0016494 A1 * | 2/2002 | Yoneda et al. ................. 560/207 |

FOREIGN PATENT DOCUMENTS

| CA | 1 215 069 | 12/1986 |
|---|---|---|
| GB | 2152030 | 7/1985 |
| JP | 04-053509 | 8/1992 |
| JP | 2000-088826 | 3/2000 |
| JP | 2003-083946 | 3/2003 |

OTHER PUBLICATIONS

Lehninger "Biochemistry" (1975) (Worth Publishers, Inc.: New York, NY) p. 75-76.*

* cited by examiner

*Primary Examiner* — Susan Hanley
(74) *Attorney, Agent, or Firm* — Kenneth H. Sonnenfeld; King & Spalding

(57) ABSTRACT

In the method for separating and purifying histidine from a culture containing the amino acid, the culture containing histidine and microbial cells is charged onto the top of a column filled with a carrier particle whose particle size is 420 µm or more and which has an ability to adsorb histidine and then an eluent is passed through the column whereby accomplishing the separation and purification of histidine, and preferably in the step mentioned above, a strong acid cation exchange resin is employed as a carrier particle whereby accomplishing the separation and purification of histidine.

2 Claims, No Drawings

METHOD FOR PURIFYING HISTIDINE FROM A CELL CULTURE

PRIORITY CLAIM

This application is a National Stage Entry of PCT/JP2007/055190, filed on Mar. 15, 2007, which claims priority to Japanese Patent Application 2006-071576, filed on Mar. 15, 2006.

TECHNICAL FIELD

The present invention relates to the method for purifying an amino acid.

BACKGROUND ART

As the method for separating and purifying an amino acid produced by fermentation from a culture, a method in which a culture of which solid components such as microbial cells have been removed by centrifugation, condensing precipitation using a polymeric condensing precipitator or ultrafiltration and the like is charged onto an ion exchange resin to allow an amino acid to be adsorbed on the resin and then the amino acid is eluted is known (Patent Reference 1), and it is essential for this method to involve pretreatment for removing the microbial cells from the culture before the culture is brought into contact with the ion exchange resin.

The method in which a culture containing microbial cells is charged onto the top of a column filled with an ion exchange resin to allow an amino acid to be adsorbed on the resin and then water is poured into the column via the bottom thereof to allow the cells to be deposited on the resin, to float up and to be removed via the top of the column and then the amino acid is eluted is also known (Patent Reference 2), and it has a disadvantageously poor amino acid purification efficiency since most of the cells contained in the culture together with the amino acid is deposited on the resin.

Patent Reference 1: Japanese Published Examined Patent Application No. 5050/1964
Patent Reference 2: Japanese Published Examined Patent Application No. 53509/1992

DISCLOSURE OF THE INVENTION

Problems to be Solved by the Invention

An objective of the present invention is to provide a method for purifying histidine having a high purity in a convenient and efficient manner from a culture containing microbial cells.

Means for Solving the Problems

The present invention relates to the following (1) to (3).

(1) A method for separating and purifying histidine from a culture comprising histidine, which comprises allowing a culture comprising histidine and microbial cells to be charged onto the top of a column filled with a carrier particle whose particle size is 350 μm or more and which has an ability to adsorb histidine and pass therethrough, and thereafter allowing an eluent to pass through the column, to thereby separate and purify histidine.

(2) The method according to the above (1), wherein the carrier particle is a strong acid cation exchange resin.

(3) The method according to the above (1) or (2), wherein the pH of the culture charged onto the column is 1 to 6.

EFFECT OF THE INVENTION

According to the present invention, histidine can readily and inexpensively be purified to a high purity.

BEST MODE FOR CARRYING OUT THE INVENTION

A culture containing histidine and microbial cells according to the invention may for example be a culture obtained by culturing a microorganism capable of producing histidine in a medium and so as to form and accumulate histidine in the medium.

The microorganism mentioned above may be any microorganism capable of producing histidine, and preferably a prokaryote, more preferably a bacterium. The prokaryote may for example be microorganisms belonging to the genus *Escherichia, Serratia, Bacillus, Brevibacterium, Corynebacterium, Microbacterium, Pseudomonas, Agrobacterium, Alicyclobacillus, Anabena, Anacystis, Arthrobacter, Azotobacter, Chromatium, Erwinia, Methylobacterium, Phormidium, Rhodobacter, Rhodopseudomonas, Rhodospirillum, Scenedesmus, Streptomyces, Synechoccus* or *Zymomonas*, and specifically, mention may be made of those of *Escherichia coli, Bacillus subtilis, Bacillus megaterium, Bacillus amyloliquefaciens, Bacillus coagulans, Bacillus licheniformis, Bacillus pumilus, Brevibacterium ammoniagenes, Brevibacterium immariophilum, Brevibacterium saccharolyticum, Brevibacterium flavum, Brevibacterium lactofermentum, Corynebacterium glutamicum, Corynebacterium acetoacidophilum, Microbacterium ammoniaphilum, Serratia ficaria, Serratia fonticola, Serratia liquefaciens, Serratia marcescens, Pseudomonas aeruginosa, Pseudomonas putida, Agrobacterium radiobacter, Agrobacterium rhizogenes, Agrobacterium rubi, Anabaena cylindrica, Anabaena doliolum, Anabaena flos-aquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacter iumrhodesianum, Methylobacterium extorquens, Phormidium sp. ATCC29409, Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Zymomonas mobilis* and the like.

The preferred prokaryote may for example be the bacteria belonging to the genus *Escherichia, Serratia, Bacillus, Brevibacterium, Corynebacterium, Pseudomonas* or *Streptomyces*, more preferably bacteria belonging to the genus *Escherichia*, and those which may be exemplified are the species of the abovementioned genus *Escherichia, Serratia, Bacillus,*

*Brevibacterium, Corynebacterium, Pseudomonas* or *Streptomyces*. Preferably, the species of the genus *Escherichia* can be mentioned.

Still more preferred bacteria include *Escherichia coli, Corynebacterium glutamicum, Corynebacterium ammoniagenes, Corynebacterium lactofermentum, Corynebacterium flavum, Corynebacterium efficacis, Bacillus subtilis, Bacillus megaterium, Serratia marcescens, Pseudomonas putida, Pseudomonas aeruginosa, Streptomyces coelicolor* or *Streptomyces lividans*, with *Escherichia coli* being particularly preferred.

The histidine in the present invention may be in L-form, DL-form, D-form or a mixture thereof.

The medium for culturing the microorganisms mentioned above may be any natural or synthetic medium as long as it contains carbon sources, nitrogen sources, inorganic salts, and the like which can be assimilated by the microorganism and allows the culture of the microorganism to be conducted efficiently.

The carbon sources include those capable of being assimilated by the microorganism, for example, carbohydrates such as glucose, fructose, sucrose, molasses containing these materials, starches or starch hydrolysates, organic acids such as acetic acid and propionic acid, alcohols such as ethanol and propanol and the like.

The nitrogen sources include ammonia and ammonium salts of inorganic or organic acids, such as ammonium chloride, ammonium sulfate, ammonium acetate, ammonium phosphate, other nitrogen-containing compounds as well as peptone, meat extracts, yeast extracts, corn steep liquor, casein hydrolysates, soy bean bran and soy bean bran hydrolysates, various cultured microbial cells and digested products thereof.

The inorganic salts include potassium dihydrogen phosphate, dipotassium hydrogen phosphate, magnesium phosphate, magnesium sulfate, sodium chloride, ferrous sulfate, manganese sulfate, copper sulfate, calcium carbonate and the like.

Culturing is conducted under aerobic condition, for example, by shaking culture, agitation submerged culture, etc. The culturing temperature is preferably 15 to 40° C., and the culturing time period is usually 6 hours to 14 days. The pH during culturing is maintained preferably at 4.0 to 10.0.

The carrier particle employed in the present invention may be a carrier particle having a particle size giving a space between the particles allowing the passage of a microbial cell, preferably a prokaryotic cell, more preferably a bacterial cell, still more preferably a cell of a bacterium belonging to the genus *Escherichia*, especially a cell of *Escherichia coli*, and it is not essential that the particle size is uniform.

The carrier particle may for example be a carrier particle whose particle size is 350 μm or more, preferably 400 μm or more, more preferably 420 μm or more, still more preferably 500 μm or more, the most preferably 600 μm or more. The carrier particle having the particle size mentioned above may for example be a carrier particle obtainable by subjecting carrier particles whose particle size is not uniform to a sieve of a mesh size of 0.35 mm, mm, 0.42 mm, 0.50 mm or 0.60 mm.

Although the carrier particle employed in the present invention having a particle size of 350 μm or more is not subjected to any upper limit of the particle size since a larger space between the particles make it easier for a microbial cell to pass through between the particles, a carrier containing 10% or less of particles having particle sizes of 2000 μm or more, preferably containing 10% or less of particles having particle sizes of 1500 μm or more, more preferably containing 10% or less of particles having particle sizes of 1180 μm or more may be contemplated in view of an easy handling and a better efficiency of the amino acid purification.

The carrier particle capable of adsorbing histidine employed in the present invention is not limited particularly as long as it is a carrier particle capable of separating and purifying histidine selectively from a culture which contains histidine together with by-product amino acids, sulfate ion, chloride ion and impurities such as pigments, based on the difference in adsorption between them, and is preferably a strong acid cation exchange resin.

The carrier particles mentioned above include carrier particles obtained by adjusting the particle sizes of Dowex series (HCR-S, HCR-W2, Marathon C, Monosphere 650C, MSC-1, Monosphere-88, 50Wx2, 50Wx4 and 50Wx8, and the like) from Dow Chemical Company, DIAION SK series (SK1B, SK102, SK104, SK110, SK112 and SK116, and the like) and DIAION PK series (PK204, PK208 and PK212, and the like) from Mitsubishi Chemical Corporation, and Amberlite series (IR120B, IR122, IR124 and XE-100, and the like) from Rohm and Haas.

The ion type of the strong acid cation resin can appropriately be selected.

The method for adjusting the particle size of the carrier particle mentioned above may for example be a method of obtaining the carrier particle which does not pass through the sieve with the mesh size of 0.35 mm, preferably 0.40 mm, more preferably 0.42 mm, further preferably 0.50 mm, and most preferably 0.60 mm and the like. Among the carrier particles listed above, a commercial product can be used in the present invention without adjusting the particle size when it is a carrier consisting of particles having particle sizes of 350 μm or more, such as Marathon C.

The strong acid cation exchange resin may be a gel type or a porous type, and the crosslinking degree of the resin is not limited particularly and may preferably be 4 to 16%, more preferably 6 to 10%.

The concentration of histidine in a culture upon being charged onto a column filled with a carrier particle is not limited particularly as long as histidine is solubilized. When a crystal of histidine is precipitated in the culture after completion of the culturing, the histidine crystal is dissolved by adding water, by heating or by adding an acid, or the histidine crystal is separated off, and then the culture may be charged.

While the pH of the culture to be charged onto the column is not limited particularly as long as it is a pH which allow a carrier particle employed in the present invention to adsorb histidine, it is preferably 1 to 6, more preferably 1 to 4, and the pH of the culture may be adjusted if necessary within the range specified above using an inorganic or organic acid such as hydrochloric acid, sulfuric acid, acetic acid, malic acid as well as an alkali solution such as sodium hydroxide, urea, calcium carbonate, ammonia and the like.

The column employed in the present invention may be any column employed ordinarily for purifying a chemical substance.

The amount of a carrier particle employed in the present invention may appropriately be selected depending on the histidine concentration or the pH of the culture to be charged, and may be 1 to 2 times that of the culture when the histidine concentration of the culture medium is about 10%.

In the method of the present invention, a culture containing histidine and microbial cells is charged onto the top, i.e., to the upper layer in the column bed, of a column filled with a carrier particle whose particle size is 350 μm or more and which has an ability to adsorb histidine.

The flow rate is preferably 0.3 to 10 m/h, more preferably 0.5 to 7 m/h as a linear velocity.

After passing the culture through the column, the culture remaining in the column can be washed off forcibly by pouring water and the like into the column via the top or bottom thereof, if necessary.

An eluent is charged preferably continuously onto the top of the column to elute histidine, whereby separating and purifying histidine.

While the eluent employed in the present invention is not subjected to any limitation with respect to the type and the concentration as long as it is a solution capable of eluting histidine bound to a carrier particle, it may for example be an alkaline aqueous solution such as aqueous ammonia solution or sodium hydroxide solution at a concentration of 0.2 to 6 mol/L, more preferably 0.5 to 3 mol/L.

The flow rate of the eluent as a linear velocity is preferably 0.3 to 10 m/h, more preferably 0.5 to 7 m/h.

The histidine separated and purified as described above can further be purified by means such as decoloration, concentration, and crystallization.

The carrier particle in the column after eluting histidine can be regenerated by forcing the eluent to go out of the column by pouring water or other suitable solvent into the column from the top thereof. When a strong acidic cation exchange resin is employed as a carrier particle, the column can repetitively used in the method of the present invention only by pouring water to force the eluent to go out of the column without conducting any particular resin regenerating procedure.

The present invention is further described in detail in the following Examples, which is not intended to limit the present invention.

EXAMPLE 1

Purification of L-histidine (1)

24 L of a culture containing 40 g/L of L-histidine and 4080 g on a wet basis of a microorganism belonging to the genus *Escherichia* was adjusted at pH3.0 using sulfuric acid, and charged at the linear velocity of 4.2 m/h at 30° C. onto a column (packing height of 6 m) filled with 12 L of SK1B (Mitsubishi Chemical Corporation, ammonia type) which had been sieved to remove particles having particle sizes less than 420 μm, to thereby adsorb L-histidine. Then, 10 L of water was poured into the column via the top thereof to force the culture remaining in the column to go out. At this time point, the cell removal ratio was 90%. After pouring water into the column via the bottom thereof to wash the column followed by elution with a 1 mol/L aqueous ammonia solution, 30 L of an eluted fraction was obtained.

The resultant eluted fraction was concentrated to 20 L to remove ammonia. Hydrochloric acid was added to the concentrated solution to adjust at pH3.7 and then decoloration and filtration were conducted with adding 100 g of an activated carbon and stirring for 30 minutes. Thereafter, by concentration up to 1.2 L, an L-histidine hydrochloride crystalline slurry was obtained.

After separating the crystal from said crystalline slurry using a basket-type separator, said crystal was washed with water and dried. As a result, 700 g of L-histidine hydrochloride monohydrate crystal (yield: 54%, purity: 99.9%, without contamination of cells) was obtained.

EXAMPLE 2

Purification of L-histidine (2)

First, 24 L of a culture containing 40 g/L of L-histidine and 4080 g on a wet basis of a microorganism of the genus *Escherichia* was adjusted at pH3.0 using sulfuric acid, and charged at the linear velocity of 4.2 m/h at 30° C. onto a column (packing height of 6 m) filled with 12 L of a strong acid cation exchange resin Marathon C (Dow Chemical Company, particle size: 535 to 635 μm, uniformity coefficient: 1.1 or less, ammonia type), to thereby adsorb L-histidine. Then, 10 L of water was poured into the column via the top thereof to force the culture remaining in the column to go out. At this time point, the cell removal ratio was 90%. After introducing water into the column via the bottom thereof to wash the column followed by elution with a 1 mol/L aqueous ammonia solution, 30 L of an eluted fraction was obtained.

The resultant eluted fraction was concentrated up to 20 L to remove ammonia. Hydrochloric acid was added to the concentrated solution to adjust at pH3.7 and then decoloration and filtration were conducted by adding 100 g of an activated carbon and stirring for 30 minutes. Thereafter, by concentration up to 1.2 L, an L-histidine hydrochloride crystalline slurry was obtained.

After separating the crystal from the crystalline slurry using a basket-type separator, the crystal was washed with water and dried. As a result, 700 g of L-histidine hydrochloride monohydrate crystal (yield: 54%, purity: 99.9%, without contamination of cells) was obtained.

COMPARATIVE EXAMPLE 1

Purification of L-histidine

24 L of the culture whose pH was adjusted as in Example 1 was charged onto a column (packing height of 6 m) filled with 12 L of SK1B (Mitsubishi Chemical Corporation, particle size: 297 to 1190 μm, ammonia type) whose particle size had not been adjusted by sieving under the condition similar to that in Example 1, but the column was occluded at the time when 5 L was passed through the column.

INDUSTRIAL APPLICABILITY

According to the present invention, histidine can conveniently be purified from a culture containing histidine and microbial cells.

The invention claimed is:

1. A method for separating and purifying histidine from a culture comprising histidine, which comprises:
    (a) charging a culture comprising histidine and microbial cells onto the top of a column that is filled with a strong acid cation exchange resin which consists of a carrier particle with a particle size of 420 μm or more and which has an ability to adsorb histidine and pass histidine therethrough, and
    (b) passing an eluent through the column,
    to thereby separate and purify histidine.
2. The method according to claim 1, wherein the pH of the culture charged onto the column is 1 to 6.

* * * * *